US00PP29447P2

(12) United States Plant Patent
Eveleens

(10) Patent No.: US PP29,447 P2
(45) Date of Patent: Jul. 3, 2018

(54) ***HYDRANGEA* PLANT NAMED 'HORT 09-012-05'**

(50) Latin Name: *Hydrangea macrophylla*
Varietal Denomination: Hort 09-012-05

(71) Applicants: Horteve Breeding BV, De Kwakel (NL); Kolster Holding BV, Boskoop (NL)

(72) Inventor: Cornelis Pieter Eveleens, De Kwakel (NL)

(73) Assignees: HORTEVE BREEDING B.V., Aalsmeer (NL), part interest; KOLSTER HOLDING B.V., Boskoop (NL), part interest ( * ) Notice: Subject to any disclaimer, the term of this patent is extended or adjusted under 35 U.S.C. 154(b) by 61 days.

(21) Appl. No.: 15/330,658

(22) Filed: Oct. 24, 2016

(51) Int. Cl.
*A01H 5/02* (2018.01)

(52) U.S. Cl.
USPC ..... Plt./250
CPC ..... *A01H 5/02* (2013.01)

(58) Field of Classification Search
USPC ..... Plt./250
CPC ..... A01H 5/02
See application file for complete search history.

*Primary Examiner* — Kent L Bell
(74) *Attorney, Agent, or Firm* — Penny J. Aguirre

(57) ABSTRACT

A new cultivar of *Hydrangea macrophylla* plant named 'Hort 09-012-05' that is characterized by its compact and uniform plant habit, its double sterile flowers with a large number of sepals, and its star-shaped sterile flowers with sepals that are white in color with pointed tips.

2 Drawing Sheets

Botanical classification: *Hydrangea macrophylla.*
Varietal denomination: 'Hort 09-012-05'.

CROSS REFERENCE TO A RELATED APPLICATION

This application is co-pending with a U.S. Plant Patent Applications filed with plants derived from the same breeding program that are entitled *Hydrangea* Plant Named 'Hort 10-087-01' (U.S. Plant patent application Ser. No. 15/330,657), *Hydrangea* Plant Named 'Hort 10-087-07' (U.S. Plant patent application Ser. No. 15/330,659), and *Hydrangea* Plant Named 'Hort 10-080-01' (U.S. Plant patent application Ser. No. 15/330,660).

BACKGROUND OF THE INVENTION

The present invention relates to a new and distinct cultivar of *Hydrangea macrophylla* and will be referred to hereafter by its cultivar name, 'Hort 09-012-05'. 'Hort 09-012-05' represents a new bigleaf *hydrangea*, a perennial shrub grown for landscape use.

'Hort 09-012-05' was derived from an ongoing controlled breeding program directed by the Inventor in Boskoop, The Netherlands. The objectives of the breeding program include developing new cultivars of *Hydrangea* with double flowers combined with compact plant habits and floriferous blooming habits. 'Hort 09-012-05' arose from the self-pollination of an unnamed and unpatented proprietary plant in the Inventor's breeding program, reference no. 07-110-08 in June of 2008. 'Hort 09-012-05' was selected as a single unique plant from amongst the resulting seedlings in June of 2015.

Asexual propagation of the new cultivar was first accomplished by stem cuttings by the Inventor in Boskoop, The Netherlands in July of 2011. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Hort 09-012-05' as a unique cultivar of *Hydrangea macrophylla.*

1. 'Hort 09-012-05' exhibits a compact and uniform plant habit.
2. 'Hort 09-012-05' exhibits double sterile flowers with a large number of sepals.
3. 'Hort 09-012-05' exhibits star-shaped sterile flowers with sepals that are white in color with pointed tips.

The parent of 'Hort 09-012-05', reference no. 07-110-08, differs from 'Hort 09-012-05' in being a lacecap type *hydrangea*, in having single flowers, and in having a taller overall plant habit. 'Hort 09-012-05' can be most closely compared to the *Hydrangea macrophylla* cultivars 'Hanabi' (not patented) and 'Hort 10-087-01'. 'Hanabi' is similar to 'Hort 09-012-05' in having double sterile flowers that are white in color. 'Hanabi' differs from 'Hort 09-012-05' in being a lacecap type *hydrangea*, in having much longer peduncles, and in having a taller overall plant habit. 'Hort 10-087-01' is similar to 'Hort 09-012-05' in having double star-shaped sterile flowers. 'Hort 10-087-01' differs from 'Hort 09-012-05' in having sepals that are pink in color and in slightly stronger stems. 'Hort 10-087-07' differs from 'Hort 09-012-05' in having sepals that are pink in color. 'Hort 10-080-01' differs from 'Hort 09-012-05' in having sepals that are pink in color with a lighter edge.

BRIEF DESCRIPTION OF THE DRAWINGS

The accompanying colored photographs illustrate the overall appearance and distinct characteristics of the new

*Hydrangea*. The photographs were taken of a plant two years in age as grown in a four-liter container outside under a shade screen in Boskoop, The Netherlands.

Figure 1:
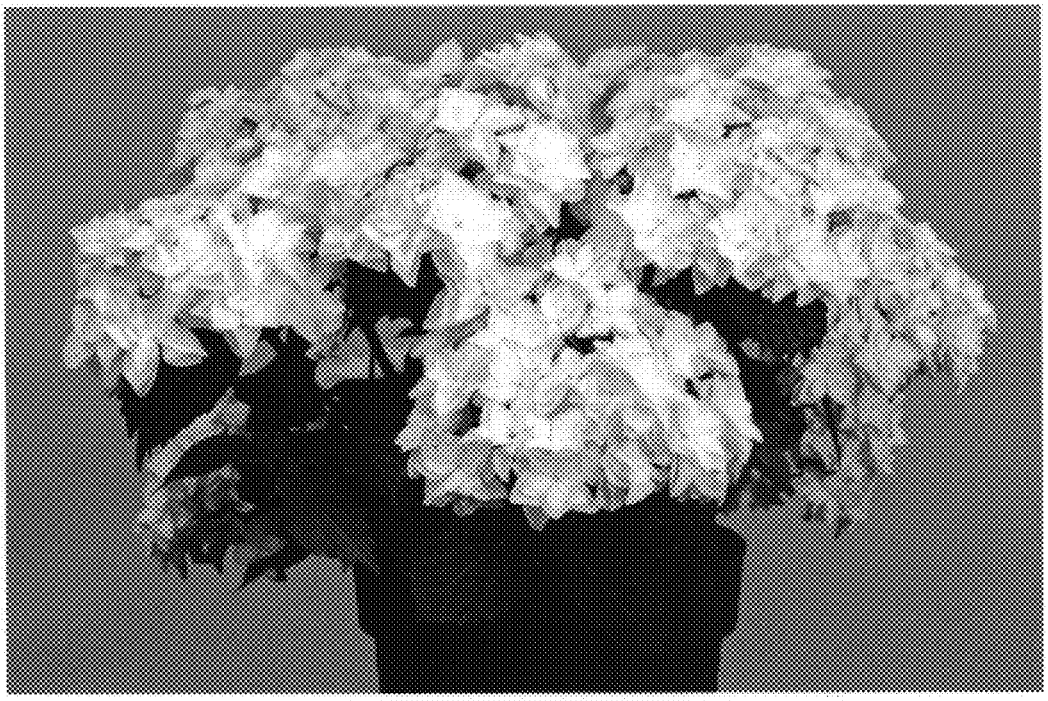

The photograph in FIG. 1 provides a side view of the plant habit of 'Hort 09-012-05' in bloom.

Figure 2:
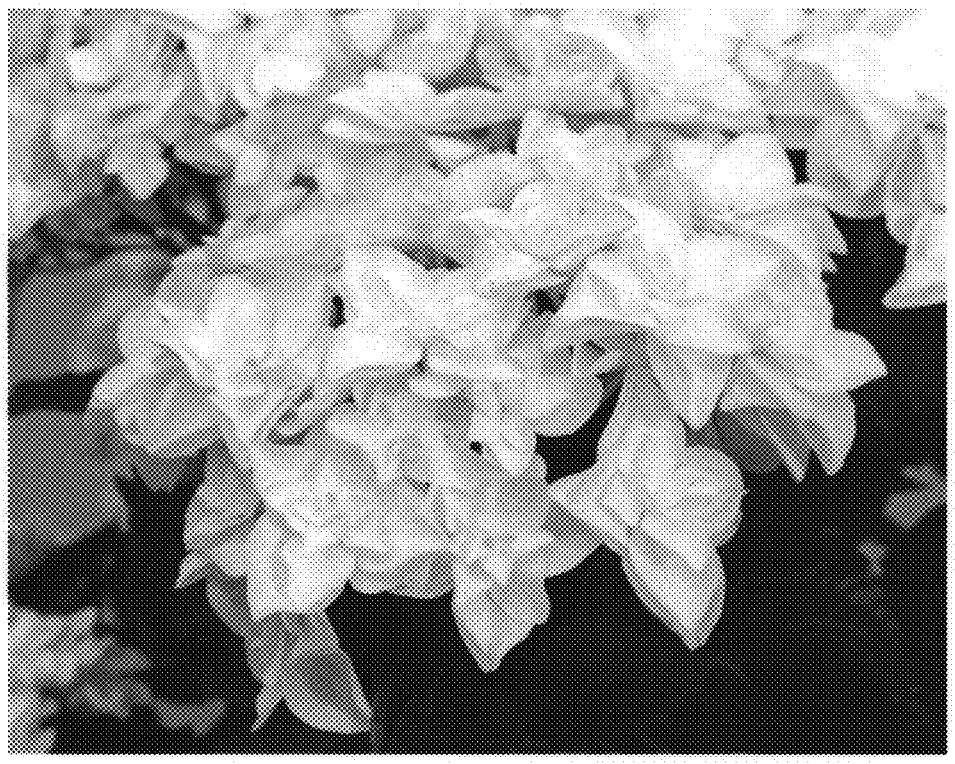

The photograph in FIG. 2 provides a close-up view of an inflorescence of 'Hort 09-012-05'.

Figure 3:
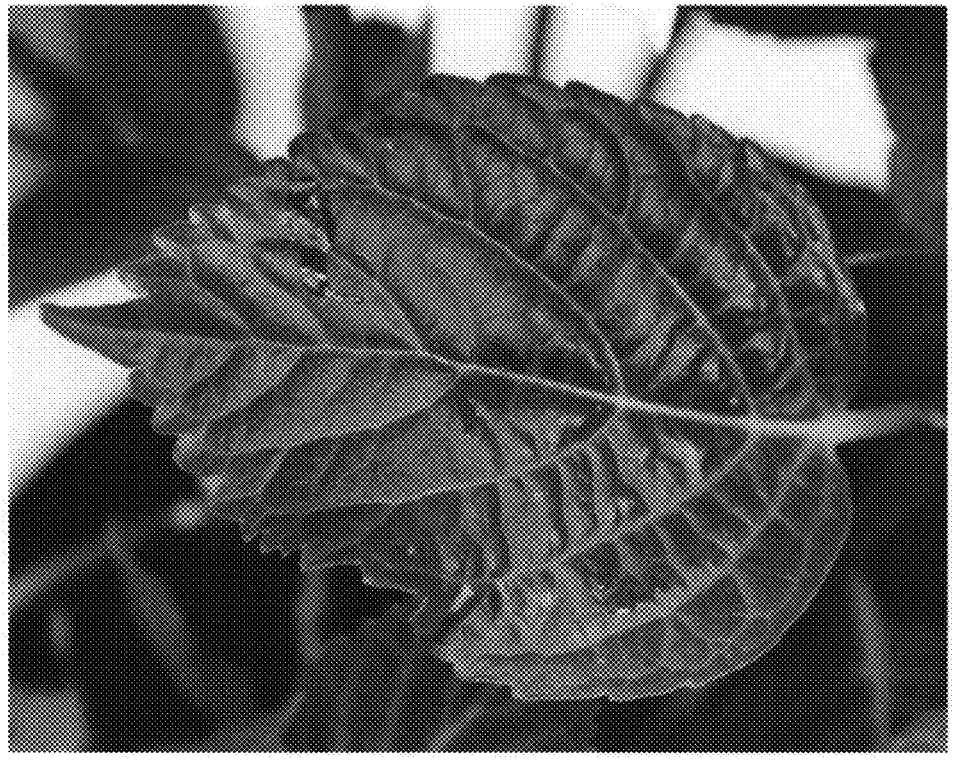

The photograph in FIG. 3 provides a close-up view of a leaf of 'Hort 09-012-05'.

The colors in the photographs are as close as possible with the photographic and printing technology utilized and the color values cited in the detailed botanical description accurately describe the colors of the new *Hydrangea*.

BOTANICAL DESCRIPTION OF THE PLANT

The following is a detailed description of plants two years in age as grown in four-liter containers outside under a shade screen in Boskoop, The Netherlands. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General description:

*Blooming period*.—From May to July in a greenhouse and from July to September outside in The Netherlands.

*Plant type*.—Perennial shrub, mophead-type *hydrangea*.

*Plant habit*.—Upright spreading, compact.

*Height and spread*.—Up to 1 m in height and 1.5 m in spread in the landscape.

*Hardiness*.—At least in U.S.D.A. Zones 5 to 9.

*Diseases and pests*.—No susceptibility and resistance to pests and diseases has been observed.

*Root description*.—Fibrous and fine, 199D in color.

*Propagation*.—Stem cuttings.

*Time required for root development*.—An average of 3.5 weeks for root initiation with a young rooted plant produced in an average of six months.

*Growth rate*.—Moderate.

Stem description:

*Stem shape*.—Rounded.

*Stem strength*.—Strong.

*Stem aspect*.—Upright to an average angle of 30° to soil.

*Stem color*.—Immature and mature stems; 144A lightly suffused with a blend between N186A and 200A at the internodes, older bark; a blend between 197B to 197C and 199C to 199D.

*Stem size*.—An average of 13.5 cm (excluding the inflorescence) in length and 5.5 mm in diameter.

*Stem surface*.—Immature and mature stems; glabrous and slightly glossy.

*Branching*.—Moderately branched with an average of 13 lateral branches, branching improves with pinching.

*Internode length*.—An average of 4.2 cm.

Foliage description:

*Leaf shape*.—Ovate to broadly ovate.

*Leaf arrangement*.—Opposite.

*Leaf division*.—Simple.

*Leaf number*.—An average of 4 (2 pairs) per lateral branch.

*Leaf base*.—Cuneate to rounded.

*Leaf apex*.—Acuminate to apiculate.

*Leaf margins*.—Serrate to dentate.

*Leaf venation*.—Pinnate, color; upper surface 144A to 144B and lower surface 145B.

*Leaf size*.—An average of 9.0 cm in length and 6.4 cm in width.

*Leaf attachment*.—Petiolate.

*Leaf surface*.—Upper surface; glabrous, moderately glossy, and moderately rugose, lower surface; glabrous, slightly glossy, and moderately rugose.

*Leaf color*.—Young leaves; upper surface 143A and lower surface 144A, mature leaves; upper surface a blend between NN137A and 147A and lower surface 147B.

*Petioles*.—Flattened, an average of 1.5 cm in length and 3 mm in width, color; upper surface 144C lightly suffused with a blend between N186A and 200A towards the stem and lower surface 144B lightly suffused with N186A and 200A towards the stem, upper surface; glabrous, smooth, and slightly glossy, lower surface; glabrous, smooth, and moderately glossy.

Inflorescence description:

*Inflorescence type*.—Flattened globular, mophead, compound corymb of rotate-shaped double sterile flowers.

*Lastingness of inflorescence*.—Sterile flowers; an average of 6 weeks, persistent, fertile flowers; an average of 3 weeks, persistent.

*Inflorescence number*.—One per lateral stem.

*Inflorescence size*.—An average of 10.8 cm in height and 16.5 cm in diameter.

*Flower number*.—An average of 44 sterile flowers and 150 fertile flowers per inflorescence.

*Flower fragrance*.—None.

*Flower aspect*.—Sterile flowers; upright to outwards and drooping, fertile flowers; upright.

*Flower size*.—Sterile flowers; an average of 5.4 cm in diameter and 2.1 cm in depth, fertile flowers; an average of 5 mm in diameter and 4 mm in depth.

*Flower shape*.—Sterile; rotate and double, fertile flowers; do not open, remain in the bud stage.

*Flower buds*.—Sterile flowers; an average of 1.1 cm in length and 6 mm in diameter, ovate in shape, color; NN155D suffused with N144D, fertile flowers; an average of 5 mm in length and 3 mm in diameter, ovate in shape, color; 157A to 157B suffused with 145A to 145B, fading to 143C in the bud stage.

*Peduncles*.—An average of 4.5 cm in length and 9 mm in diameter, held upright to outwards, 144A in color, glabrous and smooth surface, strong.

*Pedicels*.—Sterile flowers; an average of 3 cm in length and 1.5 mm in diameter, held at an average angle of 35° to peduncle, color; 144B fading to 157D near flower, strong strength, very slightly surface covered with short adpressed hairs; an average of 0.75 mm in length and NN155D in color, fertile flowers; an average of 3 mm in length and 0.75 mm in diameter, held at an average angle of 25° to peduncle, 144B to 144C in color, moderate strength, slightly glossy, smooth, and glabrous surface.

*Petals*.—Sterile and fertile flowers; not present.

*Sepals*.—Sterile flowers; an average of 20, arrangement; rotate and double in four whorls, elliptic to ovate in shape, cuneate base, acute apex, entire, undulate margin, an average of 2.3 cm in length and 1.8 cm in width, color; upper and lower surfaces when opening NN155C to NN155D, upper and lower surfaces when fully open NN155B, color fades to 145B to 145C suffused with 146C at the apex on both surfaces, upper surface; glabrous, dull, and slightly velvety, lower surface; glabrous and dull, fertile flowers; an average of 8, rotate in arrangement, ovate in shape, acute apex, cuneate base, serrate margin, an average of 3.5 mm in length and 2 mm in width, color; upper and lower surfaces a blend between 157D and 145C to 145D heavily suffused with 144C to 144D on the apical half, color does not fade, both surfaces smooth and glabrous.

Reproductive organs:

*Gynoecium*.—Sterile flowers; an average of 3 pistils, an average of 1 mm in length, stigma; club-shaped and 157D in color, style; 0.5 mm in length and 154D in color, ovary is 144C in color, fertile flowers; an average of 3 (occasionally 4 to 6), an average of 1 mm in length, stigma; club-shaped and 145D in color, style; 0.5 mm in length and 145B to 145C in color, ovary is 144C in color.

*Androecium*.—Sterile and fertile flowers; not present.

*Fruit and seed*.—No seeds or fruit observed.

It is claimed:

1. A new and distinct cultivar of *Hydrangea* plant named 'Hort 09-012-05' substantially as herein illustrated and described.

* * * * *